United States Patent [19]

Strömmer et al.

[11] Patent Number: 4,860,330
[45] Date of Patent: Aug. 22, 1989

[54] METHOD AND APPARATUS FOR MARKING A FILM WITH INFORMATION IN X-RAY PHOTOGRAPHY

[75] Inventors: Pekka Strömmer, Espoo; Arto Virta, Vantaa, both of Finland

[73] Assignee: Planmeca Oy, Finland

[21] Appl. No.: 29,315

[22] Filed: Mar. 23, 1987

[30] Foreign Application Priority Data

Mar. 21, 1986 [FI] Finland .................................. 861212

[51] Int. Cl.⁴ ............................................... H05G 1/28
[52] U.S. Cl. ..................... 378/162; 378/165; 378/166; 378/40
[58] Field of Search ............... 378/165, 162, 166, 169, 378/40, 38, 49, 163, 164; 354/105

[56] References Cited

U.S. PATENT DOCUMENTS

| | | | |
|---|---|---|---|
| 3,668,394 | 6/1972 | Panzer | 378/165 |
| 3,683,182 | 8/1972 | Farmer | 378/166 |
| 3,790,802 | 2/1974 | Mika et al. | 378/165 |
| 3,845,314 | 10/1974 | Byler et al. | 378/166 |
| 4,053,909 | 10/1977 | Shinoda et al. | 354/105 |
| 4,121,108 | 10/1978 | Manor | 378/165 |
| 4,174,481 | 11/1979 | Liebetruth | 378/165 |
| 4,507,797 | 3/1985 | Kato | 378/165 |

FOREIGN PATENT DOCUMENTS

| | | |
|---|---|---|
| 3031100 | 4/1982 | Fed. Rep. of Germany . |
| 823443 | 4/1984 | Finland . |
| 8101619 | 6/1981 | PCT Int'l Appl. . |
| 1355854 | 6/1974 | United Kingdom . |

Primary Examiner—Carolyn E. Fields
Assistant Examiner—David P. Porta
Attorney, Agent, or Firm—Steinberg & Raskin

[57] ABSTRACT

Method and apparatus for marking a film with information, e.g. patient data and other possible information in X-ray photography, such as panoramic tomography. The X-ray beam creating the X-ray photograph, and the X-ray film move in a certain manner in relation to one another. A certain area of the film is reserved for markings which are latently made thereon, to become visible when the X-ray film is developed. Markings are made simultaneously with the film exposure to the X-ray beam for the X-ray photography. The markings are sequentially made by using relative movement of the radiation with which the marking is made upon the film and the film itself, such relative movement being synchronized with the relative movement of the X-ray beam to which the film is exposed for the actual X-ray photography, and the film itself, the relative movement preferably representing a parallel deflection or displacement along a marking row.

24 Claims, 4 Drawing Sheets

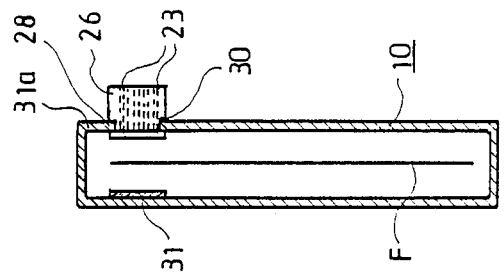
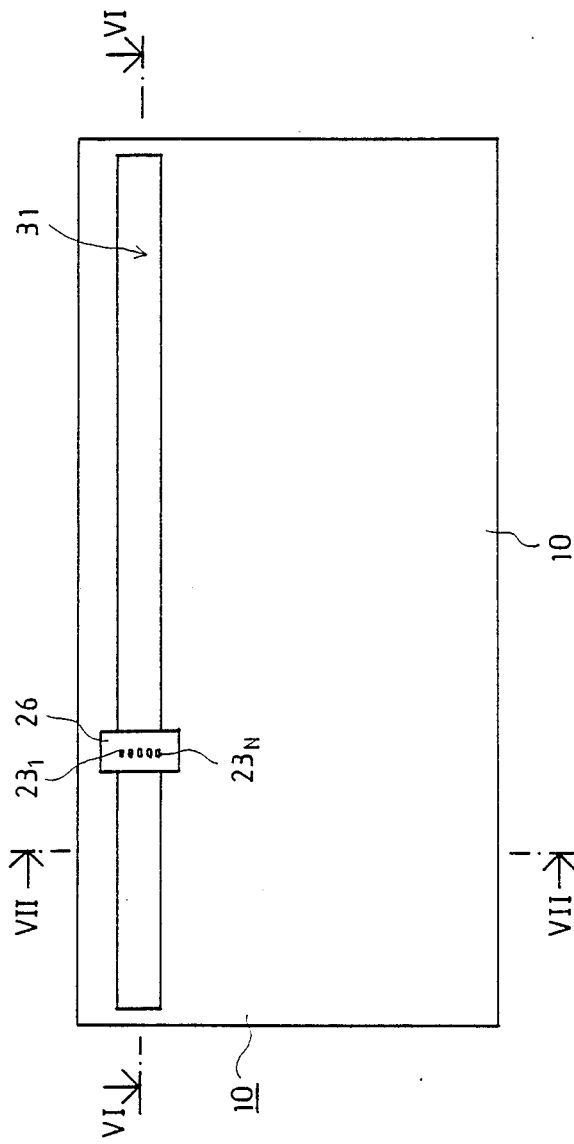
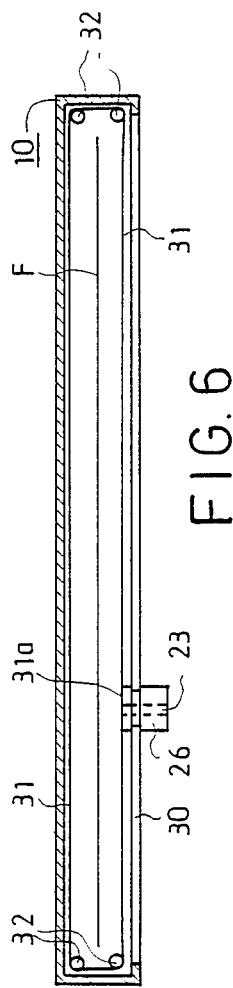
FIG. 5
FIG. 6
FIG. 7

METHOD AND APPARATUS FOR MARKING A FILM WITH INFORMATION IN X-RAY PHOTOGRAPHY

BACKGROUND OF THE INVENTION

The present invention relates to a method for marking a film with patient data and other possible information in panoramic tomography X-ray photography, in which the X-ray beam creating the X-ray photograph and the X-ray film move in a certain manner in relation to each other, and in which a certain area of the film is reserved for markings which are latently made upon the film to become visible when the X-ray film is developed.

The present invention also relates to apparatus for panoramic tomography X-ray photographing equipment, for applying the method during X-ray photography, and for marking patient data or similar information on an X-ray film, preferably on an edge area thereof, simultaneously with the exposure of the X-ray film.

X-ray photographs are usually diagnosed by someone other than the person taking the X-ray photographs. In order to be able to identify the pictures at a later time, the patient's personal data is recorded on the film after taking the actual photographs. At the same time, necessary information relating to diagnosing, exposure, and filing of the pictures, is also recorded on the film.

The laws of many countries require that the X-ray pictures must be filed. The X-ray pictures may also be voluntarily filed for follow-up studies and for possible medical examinations and care in the future.

In the prior art, the X-ray films have generally been marked manually or with a separate marking device. Usually the films are marked manually after development, by pasting a stick-on paper label upon the film, upon which the necessary data is written. A manual marking method has been writing of the data on a lead-metal tape pasted upon the surface of the film cartridge before the X-ray exposure. During the exposure, the text written on the lead tape is projected upon the X-ray film, and becomes visible when the film is developed.

The problems involved with known manual marking include material costs, the required operating time, and the danger of marking the wrong film.

In known separate marking devices, the data is written on paper and the text is projected by a light projector of the device, on an exposed but undeveloped film. The latent marking data on the film will become visible when the film is developed. The marking device is located in a room in association with the developing equipment.

Several problems have been encountered when using separate film marking devices. The device is used in a dark room which makes it inconvenient to be used. The marking strips used in the device are thrown away after a single use, which raises material cost. Marking strips are also cumbersome to handle. There is also a risk that the marking data could be confused, since the data is not written where the device is located.

Reference is made to U.S. Pat. Nos. 3,668,394; 3,683,182; 3,790,802; 3,845,314; and 4,121,108, as to the state of the art related to the present invention.

SUMMARY OF THE INVENTION

Accordingly, it is an object of the present invention to make the marking of X-ray film more reliable, more versatile, faster and simpler.

It is also an object of the present invention to provide such an X-ray film marking system, to which additional features can be feasibly added in order to make the X-ray film marking more reliable, more versatile, faster, and simpler.

These and other objects are attained by the present invention which is directed to a method for marking a film with information in X-ray photography, which comprises reserving a certain area of the film for the information to be marked thereon, moving the film and an X-ray beam creating an X-ray photograph upon the film in relation to one another, and marking the film by impact of radiation upon the reserved area thereon. The marking of the film is caused to be made simultaneously with the exposure of the film to the X-ray beam. The film is sequentially marked along a path thereon, by moving the impact of radiation marking the film along the film substantially synchronous with the relative movement of the film and the X-ray beam with respect to one another. The present invention is also directed to apparatus for marking a film with information in X-ray photography, simultaneously with the exposure of the X-ray film. In one embodiment, the apparatus comprises a secondary blind arranged between an object being photographed and the film, the secondary blind having a set of holes over a direction substantially transverse to a direction of relative movement between the film and an exposure X-ray beam, with a shutter device being provided for selectively opening and closing each hole. A control/coding unit for controlling the shutter device is also provided, such that a marking X-ray beam passing through an opened hole outlines markings upon the film in accordance with control by the control/coding unit.

In another embodiment, the apparatus for marking the film comprises a marking unit having a set of light sources, a control unit for selectively turning the light sources on and off, and a cartridge for the X-ray film which has an opening covered with a blind and elongated over a direction of relative movement between the film and an X-ray beam. A sliding rider is arranged to be movable in the opening of the cartridge, the rider having a set of openings transparent to radiation.

Therefore, the present invention is principally characterized by the markings being made simultaneously with the film exposure to an X-ray beam for X-ray photography, with the markings being made in sequence by using, the relative movement between the film itself and the radiation with which the marking is made on the film, e.g., as a deflection or displacement substantially parallel with a marking row upon the film. This relative movement is synchronized with relative movement between the film itself, and the X-ray beam to which the film is exposed for the actual X-ray photography.

One embodiment of the apparatus of the present invention is principally characterized by a secondary blind being arranged between the patient being photographed and the X-ray film, the secondary blind having a set of holes. The direction of the set of holes is substantially transverse with respect to the direction of relative movement between the film itself and the picture-creating X-ray beam. A shutter device is provided in association with the set of holes. Each hole can be opened and closed by the shutter device which is under the control of a controller/coding unit, in such a manner that an X-ray beam passing through an opened hole outlines markings upon the film according to the manner of control by the control unit.

In a second embodiment, the apparatus is principally characterized by a marking unit having a set of light sources which can be turned on and off under the control of the control unit, with a film cartridge being used in conjunction therewith having an opening covered by a blind and elongated in the direction of relative movement between the film itself and the X-ray beam. A sliding rider is provided in association with the blind, the rider being arranged to move in the groove or opening of the cartridge. A set of openings or equivalent parts which are transparent to radiation are provided in the sliding rider. This rider can be connected to the part or marking unit having the set of radiation sources.

In the present invention, the film to be marked can be exposed to either light or X-rays. The vertical deflection of the alphanumeric characters of the marking is carried out with the superimposed holes passing through the slide. X-rays or light passing through each separate hole can be timed as desired, either by opening and closing the hole, or by turning on and off a light source located in connection with each hole. The horizontal deflection is provided by linear or rotating movement of the film cartridge.

In the second embodiment of the apparatus of the invention as described above, a groove is provided along the edge of the film cartridge, in which a perforated rider or slide moves. The slide movement is synchronized with movement of a blind, in order to prevent the film from being exposed in the marking area, except through the holes in the slide or rider. When the cartridge moves, the position of the slide in the cartridge groove changes in relation to the cartridge and the film within the cartridge. The timing of the marking is synchronized with the cartridge movement. The exposure is timed and the control or synchronization of the vertical and horizontal deflections or displacement of the characters is controlled or synchronized, preferably by means of a microcomputer. The patient data is entered with a peripheral keyboard.

The device or apparatus in accordance with the present invention preferably comprises a clock which automatically records the date and time information upon the film. The X-ray generator provides the exposure parameter data, which is also automatically recorded.

The markings can also be made with X-rays in such a manner that a separate, perforated blind is arranged in the secondary blind. The vertical deflection is provided by controlled opening and closing of the superimposed holes. The movement of the cartridge is made use of for the horizontal deflection or displacement. It is possible to use standardtype cartridges in this type of system.

BRIEF DESCRIPTION OF THE DRAWINGS

The present invention will now be described in greater detail below with reference to certain exemplary embodiments thereof illustrated in the accompanying figures, to which the present invention is not intended to be restricted. In the drawings.

FIG. 5 illustrates an X-ray film cartridge used in the marking system in accordance with FIG. 4, as seen from the side of the marking groove;

FIG. 6 is a sectional view along line VI—VI in FIG. 5;

FIG. 7 is a sectional view along line VII—VII in FIG. 5; and

DESCRIPTION OF THE PREFERRED EMBODIMENTS

Figure 1:
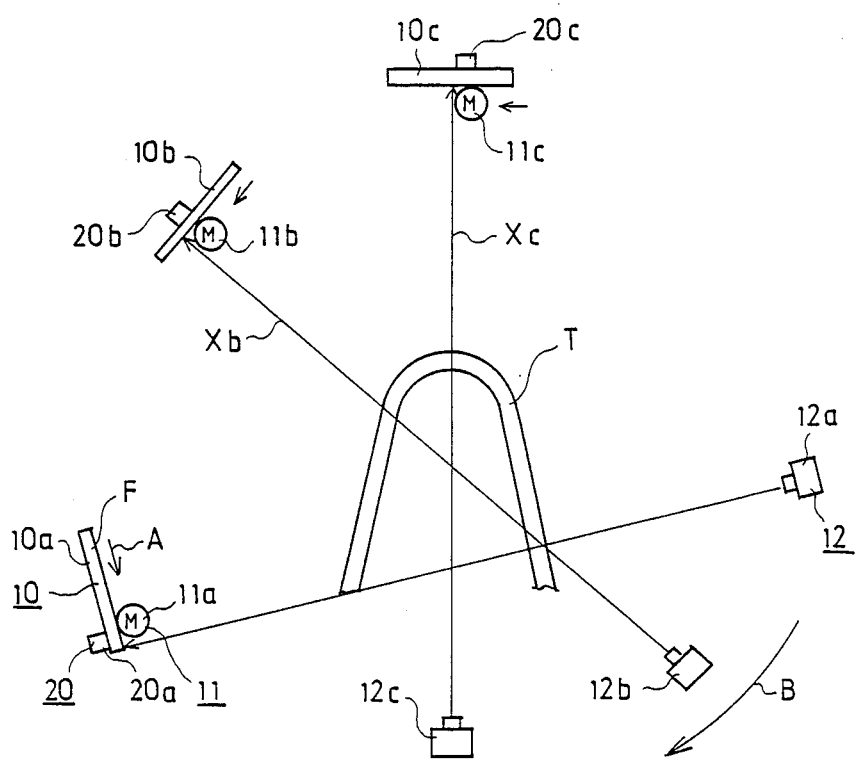
FIG. 1 is a schematic illustration of operation of panoramic tomography X-ray apparatus for dental photography.

FIG. 1 illustrates the operating principles of a panoramic tomography X-ray apparatus designed for photographing a dental arch T. The X-ray apparatus comprises an X-ray generator 12 and a film cartridge 10, a motor 11 for moving the film cartridge 10 in the direction A during exposure, and a film marking device 20 in accordance with the present invention. The X-ray generator 12 and the film cartridge 10 with the marking equipment 20 are fastened to one another with a horizontal arm or similar member, which is rotated in direction B in such a manner that upon the film within the cartridge 10, a panoramic X-ray photograph is created representing the dental arch T at the layer to which the device focused.

Reference is made to Finnish Patent Application Nos. 85-2208 (filed June 21, 1985) and 85-3524 (filed Sept. 13, 1985), as to the moving and controlling mechanisms of the X-ray generator 12 and the film cartridge 10, as well as to other details of a panoramic tomography X-ray apparatus.

The X-ray generator 12a and the film cartridge 10a in association with the same, along with the marking device 20a in association with the film cartridge 10a, begin movement from the position shown in FIG. 1 in direction B, and through an intermediate position 10b, 11b, 12b, 20b, to the middle position 10c, 11c, 12c, 20c, and further to the other end position (not illustrated). An X-ray beam $X_a$, $X_b$, $X_c$ is aimed from the X-ray generator 12a, 12b, 12c through the dental arch T, at the same time the X-ray generator 12 and the film cartridge 10 rotate about a vertical axis, and the film cartridge and the film F therewithin move in direction A driven by motor 11. A film marking device 20 in accordance with the invention is fastened to the same frame (not shown) as the motor 11. This film marking device 20, specifically during the exposure, records upon the film F the patient's personal data and also preferably necessary information related to diagnosing, exposure procedure and/or filing of photographs. A film marking system in accordance with the present invention is more closely described below.

Though the invention is illustrated in a panoramic tomography X-ray apparatus for dental photography in the application illustrated in FIG. 1, the invention may as well be applied to other tomography X-ray photography apparatus, in which there is a film cartridge which moves in relation to the X-ray beam to which the film is exposed.

Figure 2:
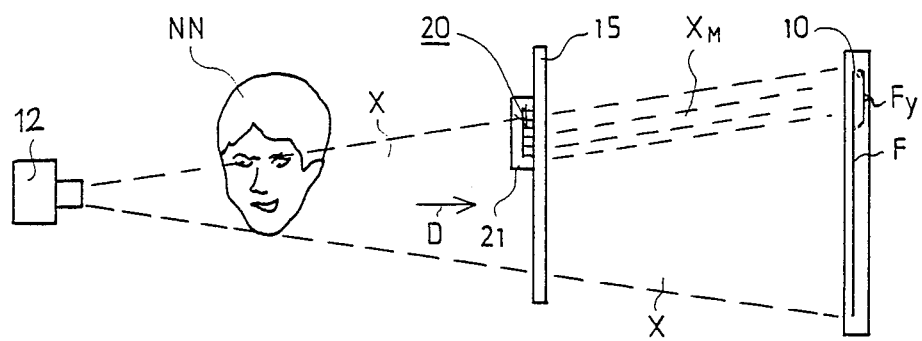
FIG. 2 is a schematic illustration of a first embodiment in accordance with the present invention.
Figure 3:
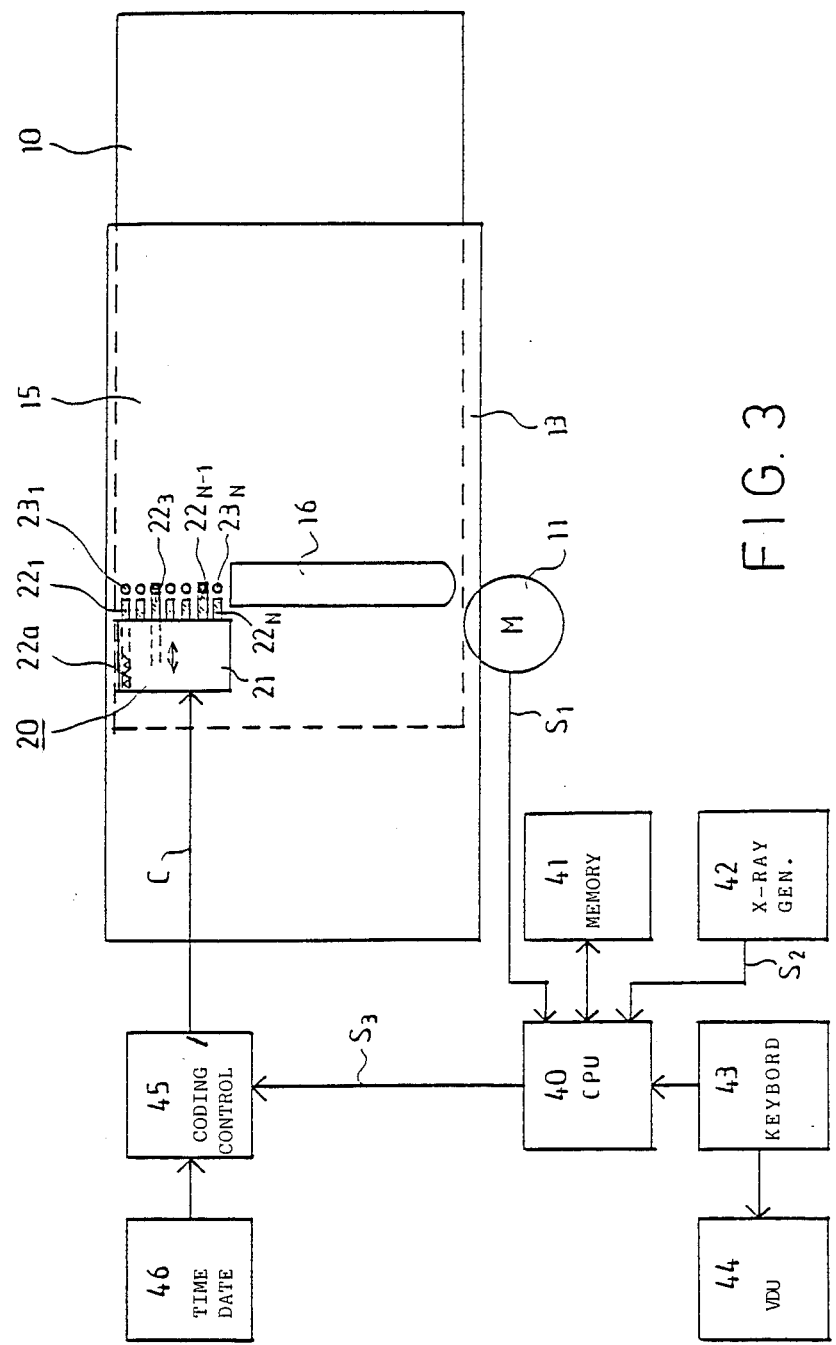
FIG. 3 is a partial block diagram presentation of apparatus as seen from direction D in FIG. 2.
Figure 4:
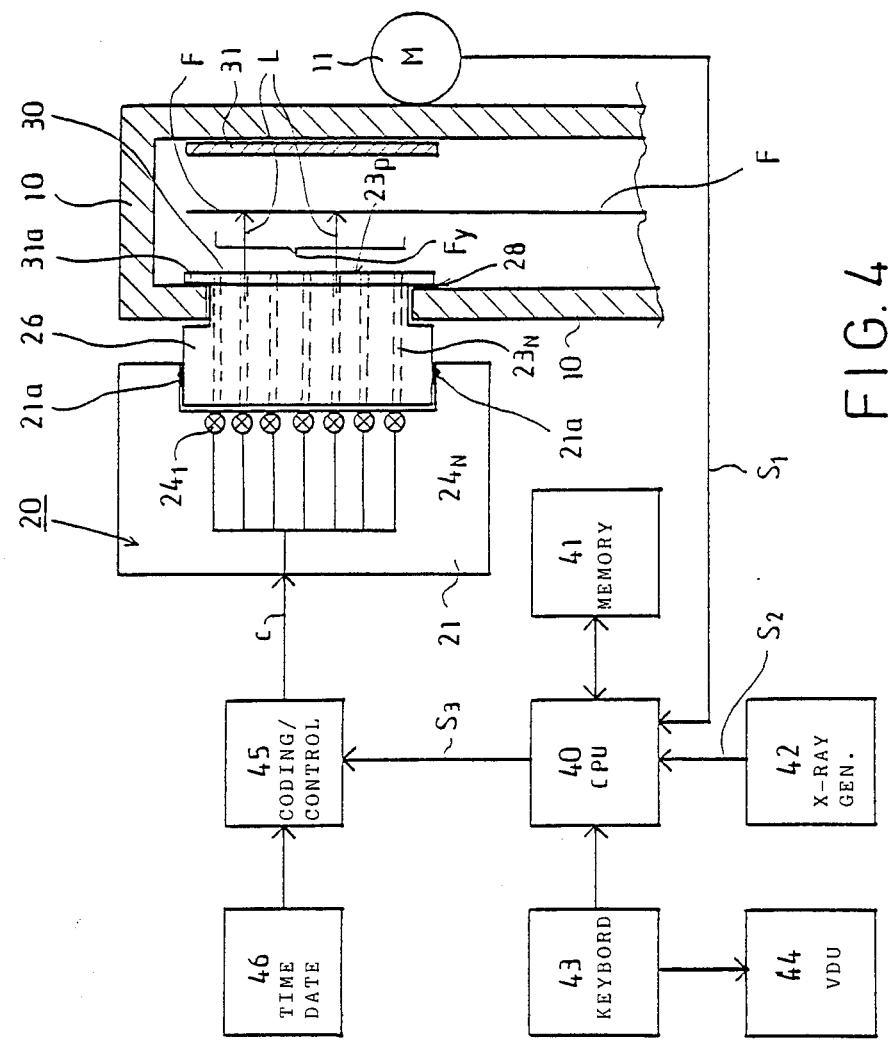
FIG. 4 is an illustration of a second embodiment of the present invention as a partial block diagram, and a partional cross-sectional view along the X-ray film cartridge.

FIGS. 2 and 3 illustrate a first embodiment of a film marking apparatus in accordance with the present invention. As shown in FIG. 2, the X-ray generator 12 aims an X-ray beam X through a patient NN. Thus, a certain layer of, for instance, the dental arch T of the patient is, in accordance with the principles illustrated in FIG. 1, photographed upon an X-ray film within the cartridge 10, the top section $F_Y$ of the film F being reserved for patient data and other relevant information. Between the film F and the patient NN, in the path of the X-ray beam X, there is a secondary blind 15 which has an opening 16 for the primary radiation beam to enter the film. In the top part of the blind 15, there is a marking device 20 in accordance with the invention, the design of which is detailed in FIG. 3.

As illustrated in FIG. 3, in association with the secondary blind 15 there is a frame section 21 of the marking device 20 having N superimposed slides $22_1$ to $22_N$. In the secondary blind there are, at slides 22, N holes $23_1$ to $23_N$ in a vertical row. In association with the frame section 21 of the marking device 20, each slide 22 has a drive mechanism (not shown), which may comprise, for example, solenoids and springs 22a holding the slides 22 in the outer position, and in which the slides $22_3$ and $22_{N-1}$ are illustrated. In an outer position, each slide 22 closes an opening 23 located thereat. When a solenoid receives a control current controlled by the coding and control unit 45(signal c), the slide 30 moves to the opened position, thus opening a hole 23 for X-rays X to enter the film F. Because the film is moving, the opened holes 23 outline or "draw" a darker trace upon the film F within the cartridge 10.

Thus, the device 20 functions as a marking device, with which the necessary markings can be made under control by the control unit 40–46. In the embodiment in accordance with FIGS. 2 and 3, the markings are outlined or "drawn" with X-rays X.

The essential feature of an apparatus in accordance with the present invention, is that the "horizontal deflection" or displacement of the marking is brought about by means of the relative movement between the radiation and the moving X-ray film F, and that the "vertical deflection" or displacement is brought about by means of a set of slides 22 and holes 23, or a similar set of holes 23 or optical cables and radiation sources 24, as illustrated in FIGS. 4 to 7. It should be noted that the expressions "vertical" deflection, deviation, or displacement and "horizontal" deviation, deflection, or displacement are used only for clarity, and in absolutely no way are bound to the directions of gravity. Therefore, the terms "vertical" and "horizontal" as used throughout the present application, merely indicate relative positioning.

The control and drive unit of the marking device illustrated in FIG. 3, comprises a central processing unit (CPU) 40, to which the signal $s_1$ from motor 11 is connected. A memory 41, a keyboard 43, and a video display unit 44 are connected to the central processing unit 40. The CPU 40 receives information about the exposure parameters from the X-ray generator 4 as a signal $s_2$. The CPU 40 controls the coding and control unit 45, by signal $s_3$, with a time and date unit 46 being connected to the coding and control unit 45. The unit 45 transmits a control signal c to the marking device 20, in accordance with the present invention which, for example, with the matrix principle illustrated in FIG. 8, outlines upon the X-ray film F the personal data typed in with the keyboard 43, the exposure parameter data provided by the signal $s_2$ from the X-ray generator 42, the time and date data provided by the unit 46, and possibly other information, for instance stored in the memory 41.

In other words, the marking is controlled by a central processing unit 40 which is preferably a microprocessor, into which the patient's personal data and similar information are entered by a keyboard 43 before the exposure, with information about the relative movement between the film F and the picture-shaping X-ray beam X controlling the marking apparatus 20 through the central processing unit 40 and coding/control (operating) unit 45, also being fed into the central processing unit 40. Exposure-parameter information is fed from the X-ray generator 42 to the central processing unit 40, for controlling the central processing unit 40 and the marking apparatus 20. When required, these parameters are recorded on the film F by exposure.

Additionally, a date/time unit 46 is connected to the central processing unit 40, and/or to the coding/control (operating) unit 45, for recording date and time information upon the film F by exposure.

FIGS. 4–7 illustrate a second embodiment of the invention, in which light (e.g. electromagnetic radiation) is used as film-marking radiation. The marking device 20 is installed in association with a groove or an opening 30 of the film cartridge 10, particularly designed for this purpose to operate as a sort of slide or rider 26, which is held in position, for instance in association with the same frame section (not illustrated) as the motor 11. In association with the rider 26, there is a blind, shaped as a closed loop, which covers the opening 30 of the cartridge 11 and prevents the film F from being exposed to light through the opening 30. The blind 31 is arranged within the cartridge 10 as a close loop to run around guides 32. When the cartridge 10, driven by the motor 11, moves, and the rider 26 of the marking device 20 is fastened to a fixed frame, then the rider 26 moves in relation to film F at the same speed as the X-ray beam X moves in relation to the film F.

The marking device illustrated in FIGS. 4–7, comprises a separate part 21, which can be fastened to the rider 26 associated with the cartridge 10, through fast-couplings 21a. The rider 26 is fastened so as to move in a groove 28 in association with the groove or opening 30 of the cartridge 10. The rider 26 is fastened to the blind 31 at 31a.

The rider 26 has a set of holes $23_1$ to $23_N$, this set of N holes being positioned crosswise or transverse to the moving direction of the rider 26. In the separate part 21 of the marking device 20, there is a set of lamps $24_1$ to $24_N$ located at the outer mouths of the holes 23 of the rider 26, when the part 21 is, with fast-couplings 21a, fastened in association with the rider 26 of the cartridge 10 as illustrated. The inner ends 23p of the holes 23 open near the film F, so that, when turned on, lamps 24 outline with light beams L markings upon the top part $F_y$ of the film F, this top part $F_y$ being specifically reserved for this purpose. When required, there is an optical system in association with holes 23, with which the light beams L are focused onto the film F. One can also use optical fibers in the device 20, so that the light sources 24 may themselves be in the outer part of the rider 26. The unit 20 with the light source 24 may be located fixedly outside of the rider 26. In this case, there is an optical cable between the unit 21 and the rider 26 which is connected to the rider 26 and the holes 23 thereof, with a connector known as such, for example, a threaded connector corresponding to the fast-coupling 21a illustrated in FIG. 4.

The lamps $24_1$ to $24_N$ are turned on and off with the coding/control unit 45. The marking and control equipment also comprises the units 40-46 described in association with FIG. 3 above.

In accordance with the present invention, the markings are outlined upon the film F with X-ray radiation (FIGS. 1 and 2) or with some other type of radiation, for instance light (FIGS. 4 to 7). The markings are preferably made in a single row, which is substantially parallel to the relative movement of X-ray film F and the X-ray beam. The marking is also made simultaneously with the photographing exposure. The exposure parameters and other data are automatically received from the central unit 40, and the variable data, for instance the patient's personal data, are typed into the system with a keyboard 43 specifically before the exposure.

Figure 8:
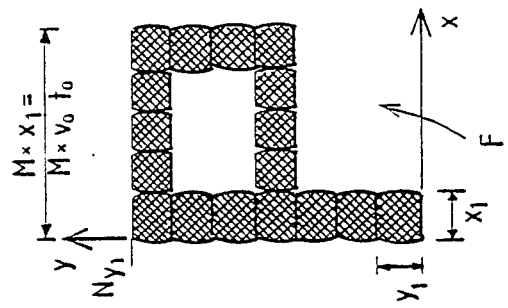
FIG. 8 illustrates the principle of a character matrix formed in a marking system in accordance with the invention.

FIG. 8 illustrates character P which is formed in accordance with the invention as a matrix $M \times N = 5 \times 7$, and in which the "horizontal deflection" is provided as the relative movement of the radiation source X or L and the film F, while the "vertical deflection" is provided by means of the open/closed or on/off control of the holes of the hole row 23.

In FIG. 8, the size of an element of the matrix is $x_1 \times y_1$. Thus, the size of the character is $Ny_1 \times Mx_1$. The direction x corresponds to the direction of the relative movement of the X-ray radiation or light radiation to which the film F is exposed. Therefore, if the velocity of the movement is $= v_0$ and the time reserved for an element $x_1$ of the character is $= t_0$, then the length of the character in the direction of a marking line is $= M \times v_0 t_0$. The normal space between characters is arranged to be, for instance, $2 \times x_1$.

The markings can also be made on more than one line, for example on two or three lines. The entire length of the top edge $F_y$ of the film F or part of the same is reserved for the markings.

Markings made in accordance with the present invention will be latently outlined upon the film F by means of radiation X or L. As the film F is normally developed, the markings will become darker than the surroundings and visible, and will remain visible.

It is a characteristic of the present invention that, for instance, patient data may be typed in with keyboard 43 before the exposure, while other parameters, for example exposure parameters, will be moved to the CPU 40 or memory 41 after setting these parameters or during the exposure. In any case, all markings are transferred in an order in accordance with the invention specifically during the exposure, when the film moves in relation to the X-ray beam. In the invention, this is called "horizontal deflection" or displacement, which, as stated above, is in no way bound to the direction of gravity.

Although the invention has been described above by an exemplary embodiment in which the film F and its cartridge 10 move linearly in relation to the X-ray beam X to which the film is being exposed, the present invention may as well be applied in such known equipment in which the film and its cartridge rotate around a certain axis being simultaneously exposed to an X-ray beam.

The present invention is by no means restricted to the aforementioned details which are described only as examples. The present invention may vary within the framework of the inventive concept as set forth above.

What is claimed is:

1. Method for marking a film with information in X-ray photography, comprising the steps of
   reserving a certain area of the film for the information to be marked thereon,
   moving the film and an X-ray beam creating an X-ray photograph upon the film in relation to one another,
   marking the film by impact of light radiation upon the reserved area thereon,
   causing the marking of the film to be made simultaneously with exposure of the film to the X-ray beam, and
   sequentially marking the film along a path thereon by moving the impact of the radiation marking the film along the film substantially synchronous with the relative movement of the film and X-ray beam with respect to one another.

2. The method of claim 1, comprising the additional step of
   controlling marking of the film in a direction substantially perpendicular to the relative movement between the film and the marking radiation, by
   providing a matrix having holes over the film, and
   selectively illuminating the respective holes in the matrix.

3. Method for marking a film with information in X-ray photography, comprising the steps of
   reserving a certain area of the film for the information to be marked thereon,
   moving the film and an X-ray beam creating an X-ray photograph upon the film in relation to one another,
   marking the film by impact of radiation upon the reserved area thereon,
   causing the marking of the film to be made simultaneously with exposure of the film to the X-ray beam,
   sequentially marking the film along a path thereon by moving the impact of the radiation marking the film along the film substantially synchronous with the relative movement of the film and X-ray beam with respect to one another,
   controlling marking of the film in a direction substantially perpendicular to the relative movement between the film and the marking radiation, by
   providing a matrix having holes over the film, and
   selectively covering and uncovering the holes in the matrix.

4. The method of claim 3, comprising the additional steps of
   situating the matrix as a secondary blind between the film and an object being photographed, and
   utilizing, as the marking radiation, a portion of the X-ray beam.

5. The method of claim 4, wherein an edge of the X-ray
   is so utilized.

6. The method of claim 3, comprising the additional steps of
   movably situating the matrix on a cartridge holding the film, and
   utilizing electromagnetic radiation as the marking radiation.

7. Method for marking a film with information in X-ray photography, comprising the steps of reserving a certain area of the film for the information to be marked thereon, moving the film and an X-ray beam creating an X-ray photograph upon the film in relation to one another, marking the film by impact of radiation upon the reserved area thereon, causing the marking of the film to be made simultaneously with exposure of the film to the X-ray beam, sequentially marking the film along a path thereon by moving the impact of the radiation marking the film along the film substantially synchronous with the relative movement of the film and X-ray beam with respect to one another, controlling the marking by entering the information into a central processing unit before the exposure of the film to the X-rays, feeding data concerning the relative movement between the film and X-ray beam to the central processing unit, said central processing unit controlling a coding and control unit which in turn outlines the information to be marked upon the film.

8. The method of claim 7, wherein the central processing unit is a microprocessor, the information to be marked includes personal data about a patient, and the information is entered into the microprocessor by a keyboard.

9. The method of claim 7, additionally comprising feeding exposure parameter information from an X-ray generator to the central processing unit for controlling the central processing unit and thereby controlling the exposure of the reserved area of the film to be marked.

10. The method of claim 9, comprising the additional step of
marking the exposure parameter information upon the film.

11. The method of claim 7, comprising the additional step of
connecting a date/time unit to the central processing unit or to the coding control unit for recording date and time information upon the film by exposure.

12. Apparatus for marking a film with information in X-ray photography, simultaneously with exposure of the film, comprising
a secondary blind situated between an object to be photographed and the film,
said secondary blind comprising a set of holes over a direction substantially transverse with respect to a direction of relative movement between the film and an exposure X-ray beam,
a shutter device for selectively opening and closing each said hole,
a control/coding unit for controlling said shutter device such that a marking X-ray beam passing through an opened hole outlines markings upon the film in accordance with control by said control/coding unit.

13. The apparatus of claim 12, wherein said secondary blind is positioned so that an edge area of the film is marked.

14. The apparatus of claim 12, wherein said secondary blind additionally comprises
an opening for exposure of the film to the exposure X-Ray beam.

15. The apparatus of claim 13, wherein the marking X-ray beam is a portion of the exposure X-ray beam.

16. An apparatus for marking a film with information in X-ray photography, simultaneously with exposure of the film, comprising
a marking unit having a set of light sources,
a control unit for selectively turning the light sources on and off,
a cartridge for the film, having an opening covered with a blind and elongated over a direction of relative movement between the film and an X-ray beam,
a sliding rider arranged to be movable in the opening of the cartridge, said rider having a set of openings transparent to radiation.

17. The apparatus of claim 16, wherein said set of openings in said rider correspond to said set of light sources in said marking unit.

18. The apparatus of claim 16, wherein said rider is connected to said blind.

19. The apparatus of claim 16, wherein said rider and marking unit are coupled to one another.

20. The apparatus of claim 16, wherein said blind is arranged in said film cartridge as a closed, movable loop about guides located near ends of said cartridge, said blind arranged to surround the film.

21. The apparatus of claim 20, wherein said blind surrounds an edge of the film.

22. The apparatus of claim 12, wherein said control/coding unit comprises
a central processing unit,
a memory coupled to said central processing unit,
a keyboard coupled to said central processing unit, an operating unit for operating said shutter device and coupled to said central processing unit, and
a date and time unit coupled to said operating unit.

23. The apparatus of claim 16, wherein said control unit comprises
a central processing unit,
a memory coupled to said central processing unit,
a keyboard coupled to said central processing unit,
an operating unit for turning said light sources on and off, and coupled to said central processing unit, and
a date and time unit coupled to said operating unit.

24. The apparatus of claim 16, wherein said rider is arranged to be movable substantially at the same speed as the relative movement between the X-ray beam and film.

* * * * *